(12) United States Patent
Cho et al.

(10) Patent No.: US 11,000,455 B2
(45) Date of Patent: May 11, 2021

(54) METHOD FOR FILLING MULTIPLE COLORS OF LIQUID COLOR COSMETIC MATERIALS, AND MULTIPLE-COLOR LIQUID COLOR COSMETIC MANUFACTURED BY USING SAME

(71) Applicant: COSMECCA KOREA CO., LTD.

(72) Inventors: Hyun Dae Cho, Cheongju-si (KR); Jong Gun Kim, Icheon-si (KR); Hyoun Cheol An, Cheongju-si (KR); Byoung Moon Kim, Suwon-si (KR); Eun Ji Kim, Seongnam-si (KR); Goo Ho Kwon, Gwangju-si (KR); Bong Jun Kim, Yongin-si (KR)

(73) Assignee: COSMECCA KOREA CO., LTD., Chungcheongbuk-Do (KR)

( * ) Notice: Subject to any disclaimer, the term of this patent is extended or adjusted under 35 U.S.C. 154(b) by 0 days.

(21) Appl. No.: 15/532,682

(22) PCT Filed: Jun. 26, 2015

(86) PCT No.: PCT/KR2015/006539
§ 371 (c)(1),
(2) Date: Jun. 2, 2017

(87) PCT Pub. No.: WO2016/204329
PCT Pub. Date: Dec. 22, 2016

(65) Prior Publication Data
US 2018/0015005 A1 Jan. 18, 2018

(30) Foreign Application Priority Data
Jun. 16, 2015 (KR) .................. 10-2015-0085032

(51) Int. Cl.
*A61K 8/02* (2006.01)
*A61Q 1/02* (2006.01)
*A61K 8/87* (2006.01)
*A45D 34/00* (2006.01)

(52) U.S. Cl.
CPC ............... *A61K 8/02* (2013.01); *A45D 34/00* (2013.01); *A61K 8/0204* (2013.01); *A61K 8/87* (2013.01); *A61Q 1/02* (2013.01); *A45D 2034/007* (2013.01); *A61K 2800/42* (2013.01); *A61K 2800/87* (2013.01)

(58) Field of Classification Search
CPC .......... A61K 8/02; A61K 8/0204; A61K 8/87; A45D 34/00; A61Q 1/02
See application file for complete search history.

(56) References Cited

U.S. PATENT DOCUMENTS

| | | | | |
|---|---|---|---|---|
| 3,566,871 | A | * 3/1971 | Richter | A61L 15/425 604/362 |
| 8,877,882 | B1 | * 11/2014 | Salamone | A61L 27/34 523/111 |
| 2012/0180808 | A1 | * 7/2012 | Nakamura | A45D 33/006 132/320 |
| 2014/0004204 | A1 | * 1/2014 | Greenhalgh | A61K 47/32 424/497 |

FOREIGN PATENT DOCUMENTS

| | | |
|---|---|---|
| KR | 10-2006-0061312 A | 6/2006 |
| KR | 10-1385652 B1 | 5/2014 |
| KR | 101385652 * | 5/2014 |
| KR | 10-2015-0017963 A | 2/2015 |
| KR | 10-1490682 B1 | 2/2015 |
| KR | 101490682 * | 2/2015 |

OTHER PUBLICATIONS

KR 101490682, published: Feb. 6, 2015; English machine translation obtained: Jun. 22, 2018.*
KR 101385652, published: May 7, 2014, English machine translation obtained: Jun. 22, 2018.*
International Search Report (ISR) dated Aug. 27, 2015, for PCT/KR2015/006539, and English translation thereof.

* cited by examiner

*Primary Examiner* — Genevieve S Alley
(74) *Attorney, Agent, or Firm* — Bacon & Thomas, PLLC

(57) ABSTRACT

A method for filling multiple colors of liquid color cosmetic materials, comprises the steps of: separating a sponge, into a plurality of sponge pieces by dividing the sponge; forming a coating film on the outer lateral side, or on the outer lateral side and on the lower surface of each of a plurality of the sponge pieces; impregnating different liquid color cosmetic materials into each of the sponge pieces having a coating film formed thereon; and fitting the angles of each of the sponge pieces, and coupling the sponge pieces. Liquid cosmetic materials having different colors are not mixed in one container without comprising a separate partition film, and a boundary line is clearly distinguished.

12 Claims, 3 Drawing Sheets

[FIG.1]
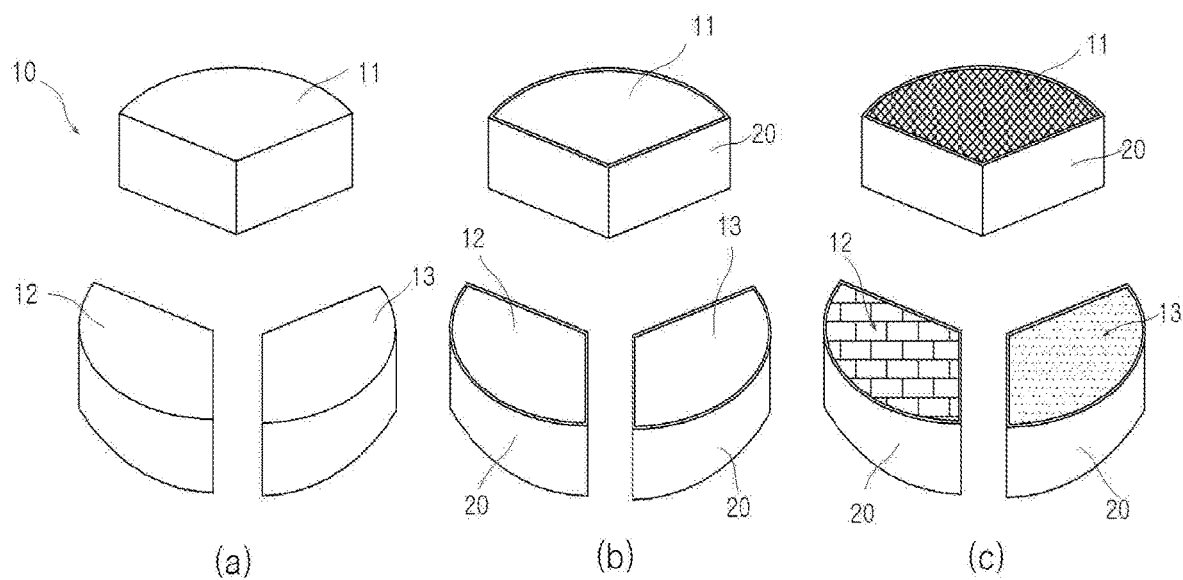

[FIG.2]
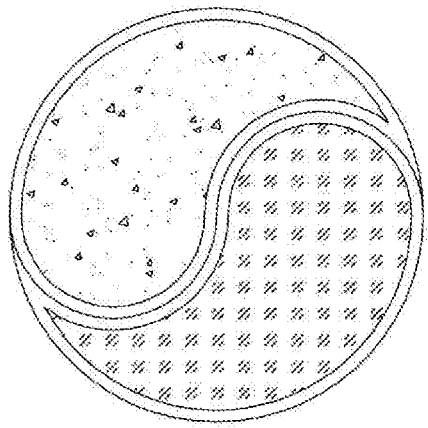
(a)
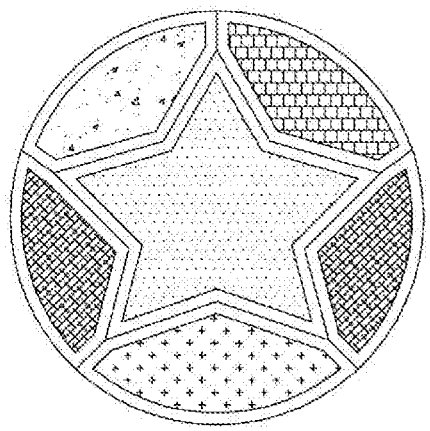
(b)
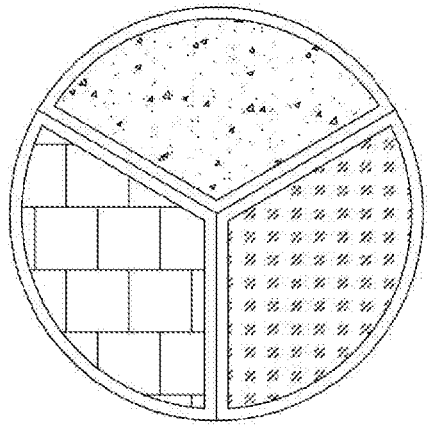
(c)
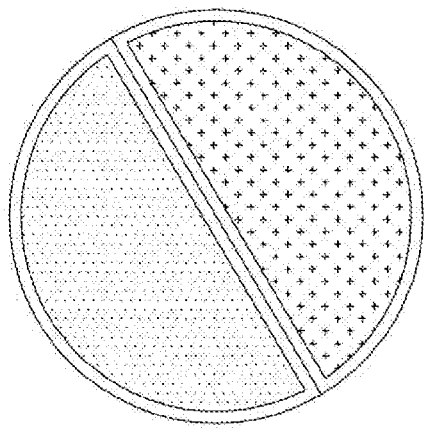
(d)

[FIG.3]
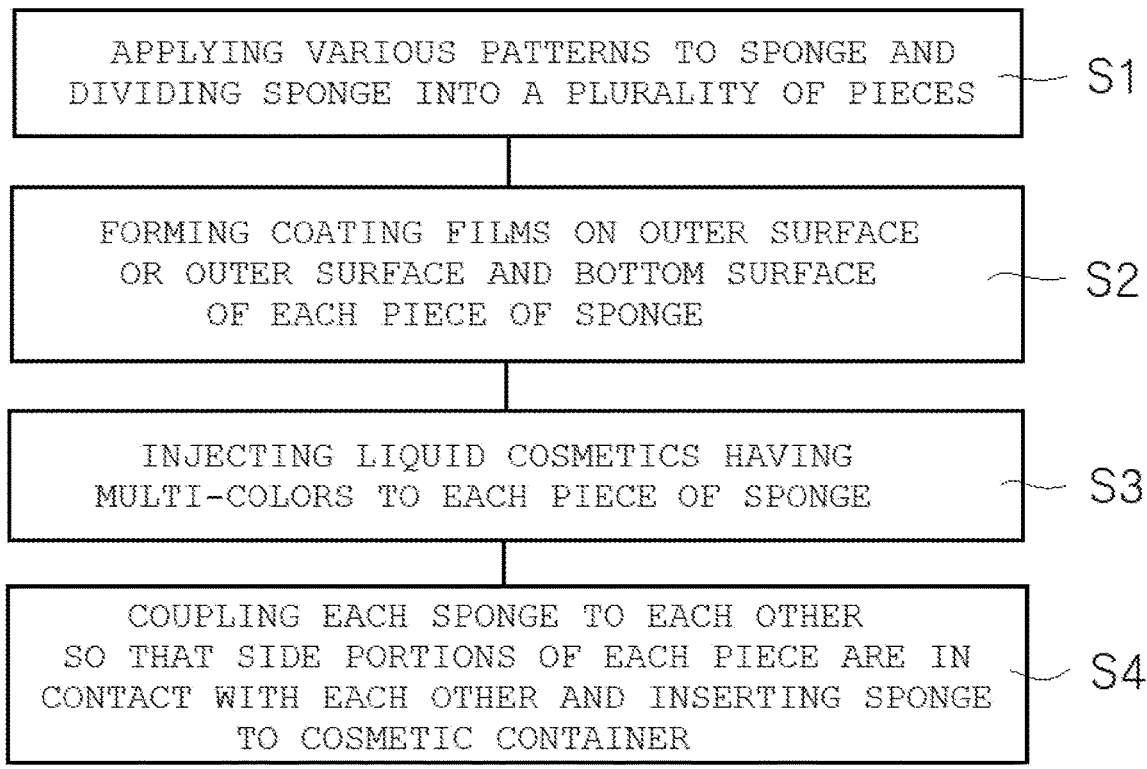

METHOD FOR FILLING MULTIPLE COLORS OF LIQUID COLOR COSMETIC MATERIALS, AND MULTIPLE-COLOR LIQUID COLOR COSMETIC MANUFACTURED BY USING SAME

BACKGROUND OF THE INVENTION

The present invention relates to a charging method of liquid cosmetics having multi-colors and a cosmetic charged with liquid cosmetics having multi-colors, and more particularly, to a method of charging cosmetics having two or more colors into one container such that cosmetics having different colors are not mixed with each other and border lines of such cosmetics are clearly divided.

BACKGROUND OF THE INVENTION

Currently, cosmetics charged with liquid cosmetics having multi-colors from among portable cosmetics are made such that cosmetics of several colors are inserted in one container for convenient carriage and storage, and a user may select one out of the cosmetics of multi-colors or mix two or more colors to create a new color.

However, the conventional cosmetics charged with liquid cosmetics having multi-colors are charged with liquid and then coagulated, and liquidity of such cosmetic causes that border lines among different colors are not clear and division among them after coagulation is not clear, making appearance of cosmetics bad. The higher liquidity of cosmetics results in the worse appearance of cosmetics.

In particular, in case of liquid cosmetics having low viscosity such as liquid eyeliner, realizing a product having multi-colors is difficult. For example, this entails a problem that, when filling red liquid cosmetic having viscosity of 5,000 cps with blue liquid cosmetic in one cosmetic container, they are mixed to be violet color.

In an attempt to solve the above problem, Korean Patent Registration No. 10-1490682 discloses that liquid cosmetics having different colors are injected to two or more sponges and they are inserted to a cosmetic container so that liquid cosmetics having different colors are not mixed and border lines therebetween is clear.

However, the aforementioned invention entails a problem that liquid cosmetics are still mixed at border lines and a bottom part of sponges where liquid cosmetics having different colors are injected.

SUMMARY OF THE INVENTION

Therefore, the present invention has been made to solve the above-mentioned problems occurring in the prior arts, and it is a first object of the present invention to provide a charging method of liquid cosmetics having multi-colors and a cosmetic charged with liquid cosmetics having multi-colors which apply patterns of predetermined shapes to a sponge made to be fit to the cosmetic container and divide the sponge into several pieces, form coating films on an outer surface or an outer surface and a bottom surface of each piece of the sponge, and inject liquid cosmetics having multi-colors to each piece of the sponge formed with the coating films so that liquid cosmetics having multi-colors are not mixed with each other and border lines therebetween are clear even without separate partitioning films.

In order to accomplish the above object, according to one exemplary embodiment of the present invention, there is provided a charging method of liquid cosmetics having multi-colors in a cosmetic container.

The charging method includes:

(S1) applying patterns of predetermined shapes to a sponge made to be fit to the cosmetic container and dividing the sponge into several pieces;

(S2) forming coating films on an outer surface or an outer surface and a bottom surface of each piece of the sponge;

(S3) injecting liquid cosmetics having multi-colors to each piece of the sponge formed with the coating films; and (S4) coupling each piece of the sponge injected with liquid cosmetics having multi-colors and injecting to the container.

Also, in the charging method,

The coating liquid in the S1 may be made by dissolving at least one coating agents selected from polyvinylpyrrolidone, polyvinyl alcohol, acrylates and acrylamide copolymer, polyurethane, rosin, wax, and silicone resin with a solvent selected from purified water, alcohol, isododecane, and mineral oil.

A mixture ratio of the coating agent to the solvent may be 10.0 wt %~90.0 wt %.

In addition, the several pieces of the sponge in the S2 may be formed by applying patterns on the sponge and dividing the sponge vertically into a top and a bottom.

The sponge is made of dry type polyurethane ether foam.

Also, a size of pores of the sponge may be between 60 and 110 ppi so as to absorb liquid cosmetics.

In the method, thickness of the coating films in the step S3 may be 0.1 μm~100 μm.

In the method, a coating liquid used to form the coating films may be made by dissolving at least one coating agents selected from polyvinylpyrrolidone, polyvinyl alcohol, acrylates and acrylamide copolymer, polyurethane, rosin, wax, and silicone resin with a solvent selected from purified water, alcohol, isododecane, and mineral oil.

A mixture ratio of the coating agent to the solvent may be 10.0 wt %~90.0 wt %.

Also, a cosmetic charged with liquid cosmetics having multi-colors according to the present invention is made by the charging method of liquid cosmetics having multi-colors.

The cosmetic according to the present invention may refer to a cosmetic with liquid having multi-colors including liquid cosmetic, the sponge injected with the liquid cosmetic, and a container inserted with the sponge.

The sponge may be formed as several pieces of the sponge applied with patterns of predetermined shapes, coating films may be formed on an outer surface or an outer surface and a bottom surface of each piece of the sponge, and liquid cosmetics having multi-colors are injected to each piece of the sponge formed with the coating films.

Also, in the cosmetic, thickness of the coating films may be 0.1 μm~100 μm.

The cosmetic according to the present invention may further include a circular ring coupled to an upper edge of the container or a cover made with a net.

According to the present invention, liquid cosmetics having different colors may not be mixed with each other in one cosmetic container and a border line therebetween is clarified even without separate partitioning films between them and thus, a user may select one out of several colors of cosmetics or mix two or more colors to create a new color.

BRIEF DESCRIPTION OF THE DRAWINGS

Further objects and advantages of the invention can be more fully understood from the following detailed description taken in conjunction with the accompanying drawings in which:

FIG. 1 is a view illustrating pieces of sponge charged with patterns of three colors which show an exemplary embodiment of the charging method, and (a) is a view illustrating a state that a sponge is divided into three pieces of a sponge, (b) is view illustrating that a coating film is formed on three pieces of a sponge, and (c) is a view that liquid cosmetics having different colors are injected to coated three pieces of sponge;

FIGS. 2(a), (b), (c) and (d) are plan views of a cosmetic charged with liquid cosmetics having multi-colors which have various patterns according to the present invention; and FIG. 3 is a flowchart of a charging method of liquid cosmetic having multi-colors according to the present invention.

DETAILED DESCRIPTION OF THE PREFERRED EMBODIMENT

The preferred embodiments of the invention will be hereinafter described in more detail with reference to the accompanying drawings.

Embodiments of the present invention will be described in more detail hereinafter with reference to the accompanying drawings. The present invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the shapes and sizes of respective elements may be exaggerated for clarity.

FIG. 1 is a view illustrating pieces of sponge charged with patterns of three colors which show an exemplary embodiment of the charging method, and (a) is a view illustrating a state that a sponge is divided into three pieces of a sponge, (b) is view illustrating that a coating film is formed on three pieces of a sponge, and (c) is a view that liquid cosmetics having different colors are injected to coated three pieces of sponge. FIGS. 2(a), (b), (c) and (d) are plan views of a cosmetic charged with liquid cosmetics having multi-colors which have various patterns according to the present invention. FIG. 3 is a flowchart of a charging method of liquid cosmetic having multi-colors according to the present invention.

As illustrated in FIGS. 1 to 3, a charging method of liquid cosmetics in a cosmetic container is as shown below.

(S1) applying patterns of predetermined shapes to a sponge made to be fit to the cosmetic container and dividing the sponge into several pieces A sponge 10 which is made to be fit to an inner shape of a container to which a sponge is to be inserted is, as illustrated in FIGS. 1 and 2, is divided to several pieces of sponge 11, 12, 13 as illustrated in FIG. 1(a) after forming desired patterns such as yin-yang shape, star shape and its peripheral part, overlapped semi circles, and three fans and so on, and are divided vertically into top and bottom portions.

At this time, the sponge 10 can be in any form of a material which is capable of absorbing liquid cosmetics. For example, it is desirable to use a sponge of dry type polyurethane ether foam.

It is desirable that pores of a sponge have a size enough to absorb liquid cosmetics, preferably 60 to 110 ppi, and more preferably 76 to 95 ppi.

(S2) forming coating films on an outer surface or an outer surface and a bottom surface of each piece of the sponge First of all, coating liquid to be used to form a coating film is prepared.

That is, the coating liquid is made by dissolving at least one coating agents selected from polyvinylpyrrolidone, polyvinyl alcohol, acrylates and acrylamide copolymer, polyurethane, rosin, wax, and silicone resin with a solvent selected from purified water, alcohol, isododecane, and mineral oil.

At this time, a mixture ratio of the coating agent to the solvent is 10.0 wt %~90.0 wt %.

Types of the coating agent and the mixture ratio between the coating agent and the solvent are determined so that, after forming a coating film on an outer surface of the sponge, the outer part of the sponge with a coating film may have the same pressure and elasticity when it is pressured vertically.

As illustrated in FIG. 1(b), the prepared coating liquid is evenly put on outer parts or outer parts and bottom parts of each piece 11, 12, 13 of the sponge using brush, roller, or spray to form a coating film 20.

In this case, it is desirable that thickness of the coating film 20 is 0.1 μm~100 μm, and more preferably, 1 μm~10 μm. If thickness of the coating film is out of the aforementioned range, if the sponge formed with a coating film is pressured vertically, side portions are not pressured well, causing inconvenience when using the sponge, and failure to successfully use liquid cosmetics injected to the sponge.

Also, the coating film 20 may have several pores having size so that liquid cosmetics injected into the sponge may not leak out. The pores of the coating film have the effect that the coating film may have elastic restoring force when pressuring the sponge vertically.

(S3) injecting liquid cosmetics having multi-colors to each piece of the sponge formed with the coating films As illustrated in FIG. 1(C), liquid cosmetics having different colors are injected to each piece of sponge 11, 12, 13 where the coating film 20 is formed.

In this case, if a coating film is formed only on an outer part of the sponge, liquid cosmetics are injected through a top or bottom portion of the sponge, and if a coating film is formed in an outer part and a lower part of the sponge, liquid cosmetics are injected through an upper part of the sponge.

(S4) coupling each piece of the sponge injected with liquid cosmetics having multi-colors and injecting to the container If liquid cosmetics having multi-colors are injected to each sponge, each sponge is coupled to each other so that side portions of each piece are in contact with each other and is inserted to a cosmetic container. In this case, if a coating film is formed on a lower part of the sponge, an upper surface without a coating film should be placed upward.

Shapes of each sponge as illustrated in FIG. 1(c) and FIG. 2 indicate that liquid cosmetics of different colors are injected.

Also, a cosmetic charged with liquid cosmetics having multi-colors is a cosmetic with liquid having multi-colors including liquid cosmetic, the sponge injected with the liquid cosmetic and a container inserted with the sponge. Here, the sponge is formed as several pieces 11, 12, 13 of sponge having predetermined patterns. At an outer part or outer part and a lower part of each piece of the sponge, the coating film 20 is formed, and to each sponge, liquid cosmetics having multi-colors are injected.

A cosmetic container has no limitation in shape, whether it is customized or general in consideration of purpose of use or preference, and a view is omitted. However, considering that a top sectional view illustrating an inner shape of a cosmetic container to which the sponge is inserted has a ring shape in general, a top view of the sponge is exemplified as a ring shape.

However, inner shape of a cosmetic container or top view of sponge are not limited to a ring shape, and can be in various shapes including rectangular, triangle, polygonal, and oval shapes.

In addition, the cosmetic in which the sponge is inserted into the cosmetic container according to the present invention may further include a circular shape ring (not shown) coupled to an upper edge of the container or a lid made of net or mesh in order to block leakage of liquid cosmetic.

While the present invention have been described in connection with the exemplary embodiments illustrated in the drawings, it will be appreciated that they are merely an illustrative embodiments and various equivalent modifications and variations of the embodiments can be made by a person having an ordinary skill in the art without departing from the spirit and scope of the present invention. Therefore, the appended claims also include such modifications and variations falling within the true technical scope of the present invention.

What is claimed is:

1. A charging method of liquid cosmetic having multi-colors in a cosmetic container, comprising the steps of:
   applying patterns of predetermined shapes to a sponge made to be fit to the cosmetic container and dividing the sponge into several pieces, wherein the several pieces of the divided sponge have at least an outer side surface that is configured in a way such that an outer side surface of at least one of the several pieces is adjacent to at least an outer side surface of at least a second one of the several pieces when the sponge is assembled as a whole;
   forming coating films on the outer side surface or the outer side surface and a bottom surface of each piece of the sponge, wherein the coating film is only coated on the outer side surface or the outer side surface and bottom surface of each piece of the sponge;
   injecting different liquid cosmetics having different colors to each piece of the sponge formed with the coating films; and
   coupling each piece of the sponge injected with the different liquid cosmetics having different colors and injecting to the container so that the outer side surfaces of the several pieces are adjacent to each other and an upper surface of each piece of the sponge without the coating film is provided in an upward application direction of the container which is accessible by a user,
   wherein the coating film formed on an outer surface of each piece of the sponge has the same pressure and elasticity with each piece of the sponge when it is pressured vertically,
   wherein the coating film formed on an outer surface of each piece of the sponge makes the cosmetics having different colors to be not mixed with each other at border lines and the border lines of such cosmetics to be clearly divided.

2. The method according to claim 1, wherein the several pieces of the sponge are formed by forming patterns on the sponge and divide the sponge vertically into a top and a bottom along the patterns, and the sponge is made of dry type polyurethane ether foam.

3. The method according to claim 2, wherein a size of pores of the sponge is between 60 and 110 ppi so as to absorb liquid cosmetics.

4. The method according to claim 1, wherein thickness of the coating film is between 0.1 µm~100 µm.

5. The method according to claim 1, wherein a coating liquid used to form the coating films is made by dissolving at least one coating agents selected from polyvinylpyrrolidone, polyvinyl alcohol, acrylates and acrylamide copolymer, polyurethane, rosin, wax, and silicone resin with a solvent selected from purified water, alcohol, isododecane, and mineral oil,
   wherein a mixture ratio of the coating agent to the solvent is 10.0 wt % to 90.0 wt %.

6. The method according to claim 1, wherein thickness of the coating film is between 1 µm-10 µm.

7. The method according to claim 1, wherein the coating film is coated by brush, roller, or spray.

8. A cosmetic charged with liquid cosmetics having multi-colors made by any of a method set forth in claim 1.

9. A cosmetic charged with liquid having multi-colors comprising:
   a liquid cosmetic,
   a sponge injected with the liquid cosmetic, and
   a container inserted with the sponge,
   wherein the sponge is formed as several pieces of the sponge applied with patterns of predetermined shapes,
   wherein the several pieces of the sponge have at least an outer side surface,
   wherein only the outer side surface or the outer surface and a bottom surface of each piece of the sponge is coated with a coating film, and
   wherein different liquid cosmetics having different colors are injected to each piece of the sponge formed with the coating films,
   wherein the coating film formed on an outer surface of each piece of the sponge has the same pressure and elasticity with each piece of the sponge when it is pressured vertically,
   wherein the coating film formed on an outer surface of each piece of the sponge makes the different liquid cosmetics having different colors to be not mixed with each other at border lines and the border lines of such cosmetics to be clearly divided, and
   wherein the sponge when placed in the container is configured in a way such that an outer side surface of at least one of the several pieces is adjacent to at least an outer side surface of at least a second one of the several pieces and an upper surface of each piece of the sponge without the coating film is provided in an upward application direction of the container which is accessible by a user.

10. The cosmetic according to claim 9, wherein thickness of the coating film is between 0.1 µm 100 µm.

11. The cosmetic according to claim 9, wherein the cosmetic further comprises a circular ring coupled to an upper edge of the container or a cover made with a net.

12. A method of charging liquid cosmetic having multi-colors in a cosmetic container, consisting the steps of:
   applying a pattern of predetermined shapes to a sponge made to be fit to the cosmetic container and dividing the sponge into multiple pieces, said multiple pieces comprising at least a first piece and a second piece;
   forming a coating film on the first piece of the sponge so that the coating film is coated on the entire first piece except for a top surface of the first piece and on the second piece of sponge so that the coating film is coated on the entire second piece except for a top surface of the second piece;

then injecting different liquid cosmetics having different colors into each of said first piece and said second piece; and then coupling each of said first piece and said second piece, and inserting into the container so that an outer side surface of the first piece is at least adjacent to an outer side surface of the second piece and the top surface without the coating film is provided in an upward direction of the container which is accessible by a user, wherein the coating film formed on an outer surface of each piece of the sponge has the same pressure and elasticity with each piece of the sponge when it is pressured vertically, wherein the coating film formed on the outer surface of each of said first piece and said second pieces makes the different liquid cosmetics having different colors to be not mixed with each other at border lines and the border lines of such cosmetics to be clearly divided.

* * * * *